United States Patent
Heikkinen

(10) Patent No.: US 6,526,308 B1
(45) Date of Patent: Feb. 25, 2003

(54) METHOD AND APPARATUS FOR CALIBRATION AND QUALITY ASSURANCE OF NUCLEAR MEDICINE IMAGING

(76) Inventor: Jari Heikkinen, Kagaminkani 10 C 20, FIN-50100 Mikkeli (FI)

( * ) Notice: Subject to any disclaimer, the term of this patent is extended or adjusted under 35 U.S.C. 154(b) by 0 days.

(21) Appl. No.: 09/763,337

(22) PCT Filed: Aug. 26, 1999

(86) PCT No.: PCT/FI99/00703

§ 371 (c)(1),
(2), (4) Date: Feb. 16, 2001

(87) PCT Pub. No.: WO00/12007

PCT Pub. Date: Mar. 9, 2000

(30) Foreign Application Priority Data

Aug. 31, 1998 (FI) .................................................. 981859

(51) Int. Cl.$^7$ ................................................. A61B 6/00
(52) U.S. Cl. ............... 600/436; 250/363.09; 250/363.1; 250/505.1; 378/147; 378/148; 378/149; 378/150; 378/151; 378/152
(58) Field of Search ...................... 600/436; 250/363.09, 250/363.1, 505.1; 378/147, 148, 149, 150, 151, 152, 153

(56) References Cited

U.S. PATENT DOCUMENTS

| | | | | |
|---|---|---|---|---|
| 5,287,273 A | * | 2/1994 | Kupfer et al. | ............... 600/436 |
| 5,299,250 A | * | 3/1994 | Styrnol et al. | ............... 378/151 |
| 5,844,962 A | * | 12/1998 | Kunert | ........................ 378/150 |
| 6,281,504 B1 | * | 8/2001 | Takayama et al. | ....... 250/363.1 |
| 6,448,560 B1 | * | 9/2002 | Tumer | ................... 250/370.09 |

* cited by examiner

Primary Examiner—Robin O. Evans
(74) Attorney, Agent, or Firm—Fasth Law Offices; Rolf Fasth

(57) ABSTRACT

A method for calibration and/or quality assurance of nuclear medicine imaging, in which functional information of the organs to be studied is achieved by inserting radioactive solution emitting detectable radiation in the organs of a phantom simulating the organs to be studied and by detecting the radiation. The filling and emptying of the organs of the phantom to be studied is simulated by regulation of the detectable radiation from the phantom. The organs to be simulated by the phantom are in form of containers filled with radioactive solution, the apparatus further comprising movable isolating parts, like steel plates, between the containers and the gamma camera to isolate radiation from the containers to the camera. The invention is also concerned with an arrangement comprising the apparatus of the invention and a gamma camera.

14 Claims, 3 Drawing Sheets

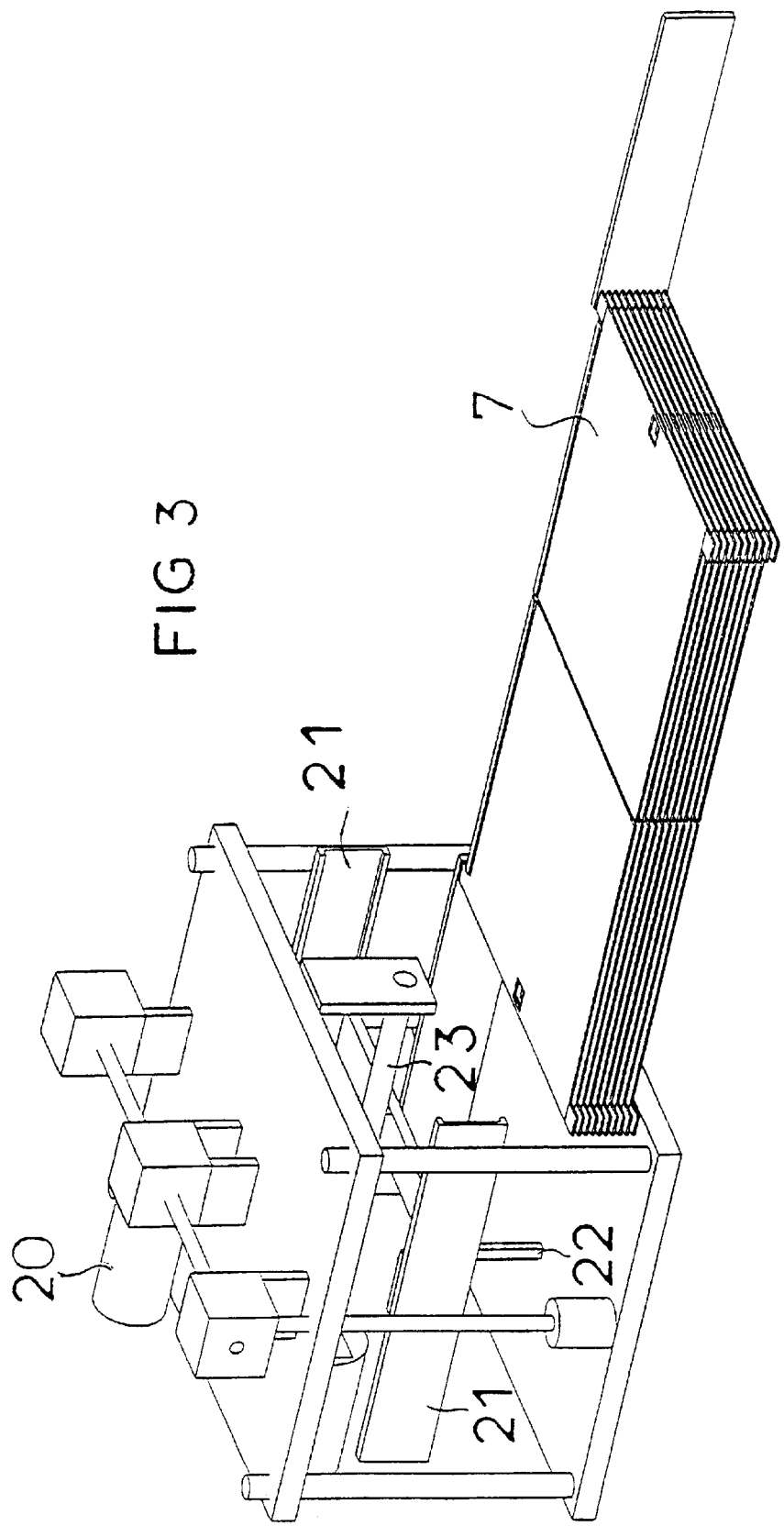

METHOD AND APPARATUS FOR CALIBRATION AND QUALITY ASSURANCE OF NUCLEAR MEDICINE IMAGING

TECHNICAL FIELD

The invention is concerned with a method and apparatus for calibration and quality assurance of nuclear medicine imaging as e.g. radionuclide renography by means of a phantom. The invention is also concerned with an arrangement comprising the apparatus of the invention.

BACKGROUND ART

The quality of nuclear medicine imaging, as in all imaging modalities, depends on the whole investigation procedure. If any of the steps is unsatisfactory, the result is not reliable. Most of the individual steps and the facility can, and should, be checked by employees of departments regularly, but this is not enough. The need for overall quality assurance by independent outside observers is taking place in medical imaging.

The basic principle of diagnostic nuclear medicine is the use of pharmaceuticals capable of carrying radionuclides that emit penetrating radiation. First the radionuclide and the pharmaceutical are combined, then the compound is injected into the circulatory system of the patient. The distribution of the radiopharmaceutical within the body can then be detected using a gamma camera to image and quantify regional physiological biochemical processes. For example dynamic radionuclide renal imaging (renography) gives functional and structural information about the kidneys and the urinary tract non-invasively.

The best way to compare the quality of imaging between laboratories is a multicentre study with a human being afflicted with known diseases. Due to ethical aspects and radiation safety it is, however, not possible. An analogue approach is to use organ-like phantoms. Zubovskii et al. (Zubovskii G A. Devishev M I, Ivanov E V, Andreeva O V and Luchkov A B 1983 Radionuclide studies with a dynamic kidney phantom *Med. Radiol.* (*Mosk*) 28 77–82 (in Russian)) have developed a renography phantom based on the flow itself of the radioactive liquid. No quantitative comparison with patient studies or repeatability of the phantom simulations exist. Neither is there presented any solutions for controlling of the flow of the radioactive solution inside the simulated organs to ensure repeatability.

Other kinds of dynamic phantoms exist. Sulab Oy in Helsinki, Finland is marketing a dynamic cardiac phantom (model DCP-101), wherein the cardiac function of the heart is simulated by moving lead shields. The degree of shielding of the radioactive ventricle area determines the ejection fraction. CAPINTEC, INC. sells a cardiac phantom (CP-201 Vanderbilt cardiac phantom), in which rotating ellipsoids simulate dynamic left atrium and verticle motion at variable heart rates. A variety of patient conditions can be simulated by varying the concentration of the radioactive solution in the ellipsoids and by adjusting the rate of rotation (variable pulse rate) and attenuator thickness. Static background represents the right heart chambers, aorta and general background tissues.

There are commercially available phantoms also for example for studying of brain perfusion single photon emission tomography (SPET) and bones but no commercially available renography phantoms for external quality assurance purposes.

An object of this invention is therefore the developing of a new phantom, with which it is possible to simulate different patient situations and organs.

Another object of this invention is the developing of a phantom, with which the flows and mixing of the radiopharmaceutical can be controlled and repeatability is possible.

SUMMARY OF THE INVENTION

To achieve the objects of the invention, there is has been developed a method for calibration and/or quality assurance of nuclear medicine imaging, in which functional information of the organs to be studied is achieved by inserting radioactive solution emitting detectable radiation in the organs of a phantom simulating the organs to be studied, and by detecting the radiation, which is mainly characterized in that the filling and emptying of the organs of the phantom to be studied is simulated by regulation of the detectable radiation from the phantom by successively removing respective adding isolating parts between the phantom and the detector of the radiation.

The arrangement of the invention mainly comprises a phantom simulating the organs to be studied and a gamma camera for detecting of the radiation and imaging of the organs. The organs to be simulated by the phantom are in form of containers filled with radioactive solution, and the phantom further comprises movable isolating parts between the containers and the gamma camera to isolate radiation from the containers to the camera.

In the preferred embodiments, the regulation of the detectable radiation is carried out in accordance with an exact time schedule to simulate a given patient situation. For example regional time activity curves over the kidneys and the heart can be used to calibrate analysis programs. The phantom can also be used in quality assurance between several laboratories by comparing clinical protocols, analysis programs and reports. The organs to be simulated by the phantom are the heart, the kidneys and/or the bladder. Additional organs to be simulated by the phantom can be the spleen, the liver, the ureters and soft tissues. The radiation is detected and imaged by a gamma camera during the simulation of the distribution of radio active solution to the body.

Before the method is started all radiation from the phantom is preferably isolated to simulate a situation before the entrance of the radio active solution to the body. The isolating is carried out by a lead plate between the phantom and the gamma camera. The method is then started by moving out the lead plate between the phantom and the gamma camera to expose the organ or organs to be studied. First, the upper body is studied and the rest of the lead plate is moved when the rest of the body is studied.

At the start of the above exposure, the radiation between the organ to be studied and the gamma camera is isolated by e.g. movable steel plates between the organ to be studied and the gamma camera. The filling/emptying of the organ to be studied is simulated by successively moving the steel plates from/to the space between the organ to be studied and the gamma camera so that the increasing of the radiation simulates the filling of the organ with radio active solution and the decreasing of the radiation simulates the emptying of the organ to be studied from radio active solution. The moving parts can be controlled by using a computerized step motor and the functions and the shapes of the kidenys can be automated.

In the method of the invention the following steps during detecting the radiation from the phantom is carried in the preferred embodiment, wherein the kidneys, the heart and the bladder is simulate:

The containers simulating the organs to be studied are filled with a radioactive solution, the lead layer between the gamma camera and the background container is pulled out to simulate the entrance of the radioactive solution to the heart, radiation from the container simulating the heart is controlled with a moving attenuator situated between the container and the gamma camera, the rest of the lead layer is pulled out, which mimics the entrance of the radiopharmaceutical to the systemic circulation, the steel plates are moved manually or automatically following an exact time schedule from the space between the kidneys and the background simulating the filling of the kidneys, after moving out of the steel plates, they are moved back to the space, simulating washout of the kidneys, after the beginning of the kidney washout, the cartridge with the tubes simulating the ureters is placed in the space between the background and the gamma camera, and finally the radiation from the container simulating the bladder is controlled with a moving attenuator to mimic filling of the bladder.

In the phantom described in this study the repeatability is good because the dynamics of the simulated kidneys depends only on mechanical movement of the steel plates. For the dame reasons the dynamics is easy to change to simulate all possible clinical situations.

The use of the phantom in tests showed its usefulness in multicentre comparisons and the phantom has a high interoperator reproducibility. The transportation of the phantom is easy in one large box and the reproduction of the phantom and the filling of the activities takes about 1–2 h. The whole phantom can be used completely by other users after a short training.

In advantageous embodiments, the moving parts can be controlled using computerized step motors. In an automated embodiment, the user only select the desired shapes and functions and presses the start buttom.

The phantom is also useful in the calibration procedure of analysis programs for dynamic radionuclide renography as well as in muiticentre comparison.

In the following, the invention is described by means of figures and some examples of preferred embodiments of the device and method of the invention. It has to be noted that the intention of the following detailed description is only for illustrative purposes and that the invention is not restricted to the details thereof. The scope of the invention is presented by the claims.

BRIEF DESCRIPTION OF FIGURES

FIG. 3 is a schematic view of a part of an automated embodiment of the invention.

DETAILED DESCRIPTION

The preferred embodiment of the arrangement of the invention comprises an apparatus with a phantom simulating organs, a gamma camera to detect radioactive radiation from the phantom and steel plates between the phantom and the gamma camera to simulate filling and emptying of radio active solution to and from the organs of the phantom. The arrangement of the invention in use is presented in FIG. 1 with reference number 1. The phantom part of the arrangement is presented in FIG. 2 with reference number 10. An example of a mechanism of the steel plates of an automated embodiment of the device of the invention is presented in FIG. 3.

Figure 1:
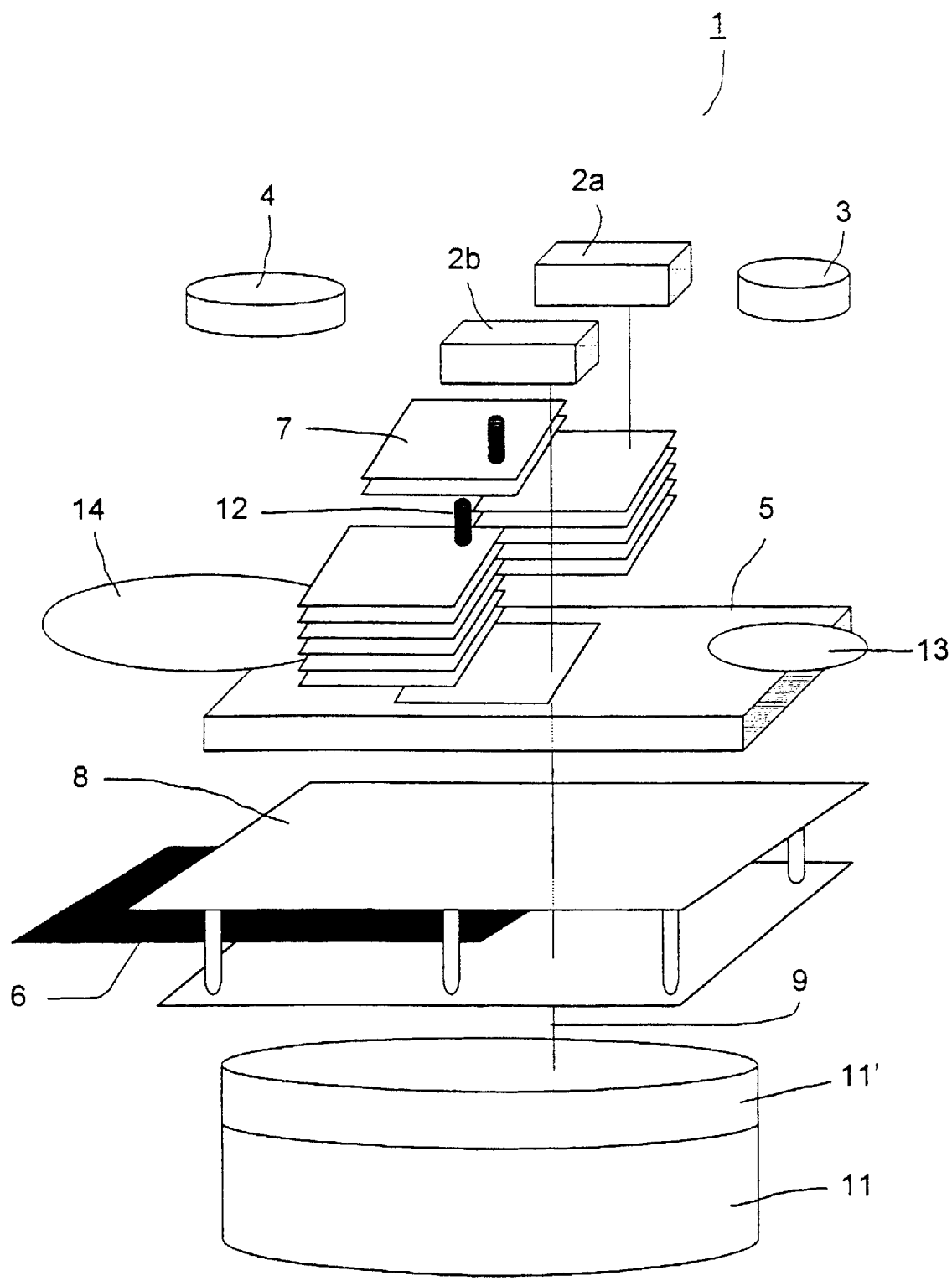
FIG. 1 is a schematic side view of the device of the invention during use.

The arrangement of the invention is presented in FIG. 1 for calibration and/or quality assurance of radionuclide renography with reference number 1. The arrangement comprises a phantom with containers simulating different organs. The containers are preferably fastened on a background cartridge or plate, but in FIG. 1 they are drawn separately of illustrative reasons.

In FIG. 1, the containers simulating the right respective the left kidney are presented with reference numbers 2a respective 2b and they are filled with a radioactive liquid. The container simulating the heart is presented with reference number 3 and the container simulating the bladder is presented with reference number 4. The phantom may comprise, in addition to the kidney containers 2a and 2b, the heart container 3 and the bladder container 4, a background container 5 simulating the shapes of the spleen, the liver and the outlines of the soft tissues for visual purposes. In that case there can be filling tubes one for the liver and one for the other parts of the background. The kidney, heart and bladder containers are covered by lead covers to hinder the penetration of radiation through other parts than through holes in the lead covers, which holes have the shapes of the simulated organs. The shapes of the organs can be seen in FIG. 2.

Figure 2:
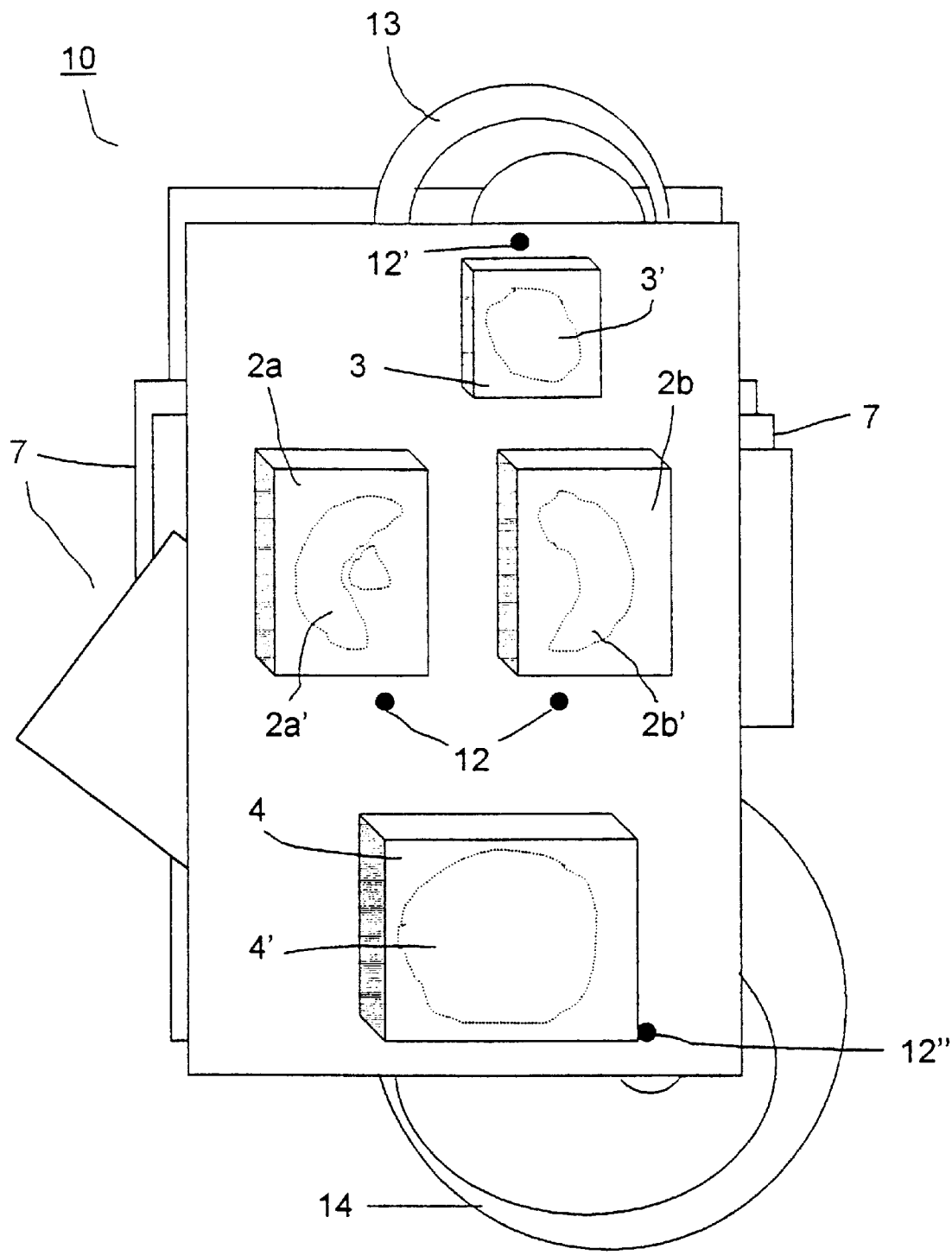
FIG. 2 is a schematic top view of the phantom of the invention.

The phantom of FIG. 1 is presented more in detail in FIG. 2 with reference number 10. In FIG. 2, it can be seen that the kidney containers 2a, 2b have kidney-shaped holes 2a', 2b' in the lead cover, the heart container 3 has a heart-shaped hole 3' in the lead cover and the bladder container 4 has a bladder-shaped hole 4' in the lead cover for the radiation. The background container 5 have shapes for other organs (not illustrated), such as for the spleen, the liver and soft tissues. There is a space, in an area of the extent of the middle body of a human being, with a thickness of 4 mm and the thickness at the spleen and the heart is about 8 mm. There is a volume to be separately filled for the liver, to achieve a difference in the imaging substances.

The apparatus of the figures also comprises a lead plate 6 between the background container 5 and the gamma camera 11 (or between the steel plates 7 and gamma camera 11 if no background container exist). The function of the lead plate 6 is to reduce radiation from the containers to the gamma camera 11 at the beginning of the examination.

If wanted, the phantom 10 also comprises a cartridge with a plastic tube filled with radioactive liquid simulating the ureters (not illustrated) to make the phantom more visual and human-like. Reference number 8 is a part made by means of plates to get a space between the camera and the background plate, so that a lead plate 6 and said cartridge could be moved in and out therein during the examination.

The functioning of the heart is simulated using an attenuator 13 for the heart container 3. The attenuator 13 (a lead disc with holes) rotates in the horizontal plane to cause a heart curve detectable by the camera. The radiation from the heart container 3 penetrates the attenuator 13 so that the gamma camera detects the distribution of the radio active solution through the heart.

There is an attenuator 14 also for the bladder container 4 acting similarly to the heart bladder 13. The radiation from the bladder container 4 penetrates the attenuator 14 so that the gamma camera can see the filling of the bladder. The attenuators can for example move round an axis 12', 12" as is illustrated in FIG. 2.

In the radionuclide renography calibration of the invention, the containers of the phantom 10 are filled with a radioactive solution, such as a $^{99m}$Tc solution. Examples of volumes and activities are shown in table 1. The activities of the containers and the cateters are made proportional to the patient dosage and the imaging liquid (the radiopharmaceutical) used by the laboratory. Then the phantom 10 is positioned on the top of the face up collimator 11' of the gamma camera 11. The lead layer 6 is between the background containers 5 and the gamma camera 11 inside the frame 8 and all the steel plates 7 are between the kidney containers 2a and 2b and the background container 5.

The gamma camera 11 is detecting the radioactive radiation 9 from the radioactive solution in the phantom and imaging the situation at routinely used time intervals. As the function of the lead plate 6 is to reduce radiation from the containers, which are simulating the organs and filled with the radioactive solution, to the gamma camera at the beginning of the examination, it simulates the situation before the entrance of the radioactive solution to the body.

At the start of the renography, at a time of about 0–5 s, the lead layer 6 between the collimator 11' and the background container 5 inside the frame 8 is pulled out ca 65 mm caudally to simulate the entrance of the radioactive liquid in the body. In other words, when the imaging starts, the lead plate is slowly moved out from the space between the phantom and the camera. The rotation of the attenuator 13 between the heart container and the gamma camera simulates the circulation of imaging agent through the heart.

The rest of the lead layer 6 is pulled out after 19 s, which mimics the entrance of the radiopharmaceutical to the systemic circulation.

Then the steel plates 7 are moved out, preferably one by one, manually or by means of an automated mechanism following an exact time schedule from the space between the kidneys 2 and the background 5. The time schedule is designed in accordance with different patient situations and/or deseases and according to the biochemical processes of the person to be studied. The moving of the steel plates 7 simulates the filling of the kidneys which can be detected by the gamma camera 11 as increasing radiation penetrating the plates as the amount of the steel plates 7 decreases between the phantom and the camera 11. The moving of the steel plates 7 can for example take place around an axis 12 as in the manual version of FIG. 1. In the manual version of the invention, the functioning of the phantom requires two persons to take care of the moving out of the steel plates 5; one for each kidney. An automated version is presented in FIG. 3. After the ca 30–40, for example 36 plates, have been moved out, they are moved back to that original space, simulating washout of the kidneys. The amount of steel plates depends on the time of the biochemical process and how often they are moved one by one.

In the beginning of the kidney washout, the cartridge with the tubes filled with radioactive liquid simulating the ureters is placed in the space between the background 5 and the gamma camera 11 inside the frame 8. Finally, there is a moving attenuator 14 between the bladder container 4 and the gamma camera 11 for simulating the filling of the bladder.

In another embodiment of the invention (which is not illustrated), there can be steel plates to simulate the entrance to and filling of the heart instead of an attenuator. Also the filling of the bladder can be simulated by means of steel plates.

FIG. 3 shows an example of an embodiment of the invention, wherein the moving of the steel plates 7 is automated. It can be generalized with a step motor 20 moving rails 21 up and down. The part 22 takes a plate, which plate is moved by 23. The mechanism can be programmed to do the steps in accordance with a certain time schedule.

EXAMPLES

The following examples with tables 1–5 was published in Heikkinen, Jari. External quality assurance of nuclear medicine imaging. Kuopio University Publications C. Natural and Environmental Sciences 89.1999. 50p.

Time-activity Curves

Sex different time schedules and kidney covers were used to simulate three clinical cases (table 2). In the first case time-activity curves of the kidneys were generated to simulate normal $^{99m}$Tc MAG3 (phantom I, left kidney) and $^{99m}$Tc DTPA (phantom I, right kidney) curves (Stabin et al 1992). The second case simulates obstruction (phantom II, left kidney) and hydronephrosis (phantom II, right kidney) and the effect of diuretics at 10 min after the beginning of the study. The curves of the third case were generated from patient studies to simulate fast (phantom III, left kidney) and slow (phantom III, right kidney) function of the kidneys.

Patient Studies

Five $^{99m}$Tc DTPA and five $^{99m}$Tc MAG3 patient studies were acquired with an Elscint Apex 409ECT gamma camera equipped with an all-purpose collimator. The first 64 images were acquired at 1 s intervals and next 192 images at 8 s intervals. The age of the DTPA patients was 66+−19 years and the injected activity was 181.3+−7.4 MBq. The MAG3 patients had an age of 61+−19 years and an injected activity of 114.7+−3.7 MBq.

Count Rates

The phantom was imaged as in the patient studies to estimate count rates. Circular (nine pixels) regions of interest (ROI) were drawn on kidneys, soft tissues (inferior to both kidneys), liver, spleen, heart and bladder. Maximum and minimum (after maximum) count rates were collected and integral calculated from the time activity curves of five $^{99m}$Tc MAG3, five $^{99m}$Tc DTPA patients and three phantom cases (table 2). Values from the patient and the phantom studies were compared by calculating correlations using a bivariate Pearson two-tailed method.

Precision and Accuracy

A Siemens Orbiter gamma camera equipped with an all-purpose collimator was used to define the precision. First 30 images were acquired at 2 s intervals and then 90 images at 20 s intervals. Data nalysis was made with the renography program of Hermes (nuclear Diagnostics AB, Hägersten, Sweden). Phantom simulations I and II (table 2) were repeated three times. The coefficient of variation (CV) of the repeated measusrments wqs calculated to express the precision error (Glüer et al 1995). The parameters $T_{max}$, $T_{1/2}$ and 20 min/max (activity at 20 min divided by the maximum activity) were estimated from the schedules and compared with the measured values obtained from phantom simulations. Accuracy was defined as a percentage difference between theoretical and measured values.

Multicentre Comparison

The simulation with the phantom was made in 19 Finnish nuclear medicine laboratories that participated in a national multicentre quality assurance survey in summer 1997. The test was organized by Labquality Ltd. All the laboratories were visited by the inventor and the containers filled with activities which produced count rates close to clinical situations; all three patientcases (table 2) were simulated in every laboratory. One person from each laboratory had to be taught to move the steel plates of the right kidney.

Results

The count rates produced by the clinical patient studies and the phantom simulations are seen in table 3. The heart, the kidneys and the bladder produced very similar count rates in the $^{99m}$Tc MAG3 patients and the phantom simulations. Time-activity integrals of the liver, the spleen and the background were also equal. With $^{99m}$Tc DTPA patients the maximum count rates are lower and the minimum count rates higher from those of the $^{m99}$Tc MAG3 patients and the phantom simulations. Although, the activity injected was higher in $^{99m}$Tc DTPA than in $^{99m}$Tc MAG3 patients, the time activity integral of the spleen and the background was higher with $^{99m}$Tc DTPA than with $^{99m}$Tc MAG3.

Precision errors are shown in table 4. The size of the regions of interest over the kidneys (area) in the analysis of repeated measurements were not exactly the same. The biggest variation was with the maximum count rate. Maximum variation of the analysed parameters was seen in MTT.

The comparison of the three measured parameters and the corresponding values estimated from the time schedules are shown in table 5. The largest differences are seen in $T_{1/2}$ with the simulations of the right kidneys.

Most of the participating laboratories gave an example of their own patient study. A visual comparison between patient and simulated phantom printouts showed a reasonable close approach. In particular a visual comparison of the produced phantom images and the curves of different laboratories seemed very similar. The percentage difference between measured and theoretical $T_{max}$ values was 6.8+−6.2%, for the simulation I left kidney 6.9+−5.2% and right kidney 6.7+−7.5% and for the simulation III 8.5+−7.6% and 5.0+−3.6% respectively. Renography sets of the phantom and the patient studies was performed with variable gamma camera systems (not illustrated).

Discussion

The materials used in the construction of the phantom were chosen for their availability price and physical properties. The containers were made or purchased from plastic and the attenuating material used was steel. Initial measurements showed that those materials were suitable when using different activities of technetium, which produce clinical count rates. The use of lead covers over the kidney containers was found to be practical. One reason for this is radiation safety for the user of the phantom and another is that the holes are easy to cut in the lead to produce kidneys of different shapes.

Embodiment of Invention

The examples were performed with a prototype of the invention, in which the function of hte kidneys were simulated by manually movable steel plates. The heart function was simulated non-inventively by filling and emptying a syringe and the bladder function was simulated by moving a bladder container cranially.

TABLE 1

Volumes and activities of the containers of the phantom simulating III MBq patient dose.

|  | Volume (ml) | Activity (MBq) |
|---|---|---|
| Kidney | 180 | 55.5† |
| Liver | 64 | 2.22 |
| Background | 420 | 7.40 |
| Heart | 30 | 4.63 |
| Ureters | 3 | 0.74 |

†The activity in the left kidney of phantom simulation II was 74 MBq.

TABLE 2

Time schedule for the three phantom simulations.

| Phantom I: left kidney | | Phantom I: right kidney | | Phantom II: left kidney | | Phantom II: right kidney | | Phantom III: left kidney | | Phantom III: right kidney | |
|---|---|---|---|---|---|---|---|---|---|---|---|
| Plate(s) (number) | time (min:s) | Plate(s) (number) | time (min:s) | Plate(s) (number) | time (min:s) | Plate(s) (number) | time (min:s) | Plate(s) (number) | time (min:s) | Plate(s) (number) | time (min:s) |
| 1–7 | 00.40 | 1–10 | 00:40 | 1–8 | 00:45 | 1–8 | 00:45 | 1–8 | 00:40 | lead plate | 00:50 |
| 8–14 | 00:50 | 11–21 | 00:50 | 9–16 | 01:00 | 9–16 | 01:00 | 9–16 | 00:50 | 1–15 | 01:00 |
| 15–28 | 01:00 | 22–31 | 01:00 | 17–21 | 01:20 | 17–21 | 01:20 | 17–24 | 01:00 | 16–22 | 01:15 |
| 29–31 | 01:40 | 32 | 01:10 | 22–24 | 01:40 | 22–24 | 01:40 | 25–27 | 01:15 | 23–24 | 01:30 |
| 32 | 02:00 | 33 | 01:20 | 25–27 | 02:00 | 25–27 | 02:00 | 28–30 | 01:30 | 25 | 02:00 |
| 33 | 02:20 | 34 | 01:40 | 28 | 02:20 | 28 | 02:15 | 31–32 | 01:45 | 26 | 02:30 |
| 34 | 02:40 | 35 | 02:05 | 29 | 02:40 | 29 | 02:30 | 33 | 02:00 | 27 | 03:00 |
| 35 | 03:20 | 36 | 02:30 | 30 | 03:00 | 30 | 02:45 | 34 | 02:20 | 28 | 03:15 |
| 36 | 04:00 |  |  | 31 | 03:30 | 31 | 03:00 | 35 | 02:40 | 29 | 03:30 |
|  |  | 1 | 03:10 | 32 | 04:00 | 32 | 03:20 | 36 | 03:00 | 30 | 03:50 |
| 1 | 05:00 | 2 | 03:50 | 33 | 05:00 | 33 | 03:40 |  |  | 31 | 04:00 |
| 2 | 06:00 | 3 | 04:30 | 34 | 07:00 | 34 | 04:20 | 1 | 03:20 | 32 | 04.20 |
| 3 | 07:20 | 4 | 05:50 | 35 | 10:00 | 35 | 05:30 | 2 | 03:40 | 33 | 05:10 |
| 4 | 08:20 | 5 | 07:10 | 36 | 14:00 | 36 | 07:00 | 3 | 04:00 | 34 | 06:00 |
| 5 | 09:20 | 6 | 09:00 | Obstruction |  | Hydronephrosis |  | 4 | 04:20 | 35 | 06:30 |
| 6 | 10:00 | 7 | 12:00 |  |  | 1 | 10:30 | 5 | 04:40 | 36 | 06:40 |
| 7 | 11:00 | 8 | 15:00 |  |  | 2 | 10:50 | 6 | 05:00 |  |  |
| 8 | 12:00 | 9 | 18:00 |  |  | 3 | 11:00 | 7 | 05:20 | 1 | 06:50 |
| 9 | 12:30 | 10 | 21:00 |  |  | 4 | 11:20 | 8 | 05:40 | 2 | 07:50 |
| 10 | 13:10 | 11 | 26:00 |  |  | 5 | 11:50 | 9 | 06:00 | 3 | 08:50 |
| 11 | 14:00 | 12 | 30:00 |  |  | 6 | 12:10 | 10 | 06:30 | 4 | 09:20 |

TABLE 2-continued

Time schedule for the three phantom simulations.

| Phantom I: left kidney | | Phantom I: right kidney | | Phantom II: left kidney | | Phantom II: right kidney | | Phantom III: left kidney | | Phantom III: right kidney | |
|---|---|---|---|---|---|---|---|---|---|---|---|
| Plate(s) (number) | time (min:s) | Plate(s) (number) | time (min:s) | Plate(s) (number) | time (min:s) | Plate(s) (number) | time (min:s) | Plate(s) (number) | time (min:s) | Plate(s) (number) | time (min:s) |
| 12 | 14:50 | | | | | 7 | 12:40 | 11 | 07:00 | 5 | 10:00 |
| 13 | 15:40 | | | | | 8 | 13:10 | 12 | 07:30 | 6 | 10:40 |
| 14 | 17:30 | | | | | 9 | 13:50 | 13 | 08:00 | 7 | 12:00 |
| 15 | 20:00 | | | | | 10 | 14:30 | 14 | 09:00 | 8 | 13:00 |
| 16 | 24:00 | | | | | 11 | 15:10 | 15 | 10:00 | 9 | 13:40 |
| 17 | 30:00 | | | | | 12 | 16:40 | 16 | 11:00 | 10 | 15:00 |
| | | | | | | 13 | 18:10 | 17 | 12:30 | 11 | 17:30 |
| | | | | | | 14 | 19:00 | 18 | 14:00 | 12 | 20:00 |
| | | | | | | 15 | 19:50 | 19 | 16:00 | 13 | 25:00 |
| | | | | | | 16 | 22:10 | 20 | 18:00 | 14 | 30:00 |
| | | | | | | 17 | 26:00 | 21 | 20:00 | | |
| | | | | | | 18 | 30:00 | 22 | 24:00 | | |
| | | | | | | | | 23 | 28:00 | | |

Lead plate = additional lead plate was placed between the kidney container and gamma camera to simulate low perfusion.

TABLE 3

Count rates from five $^{99m}$Tc MAG3, five $^{99m}$Tc DTPA and three phantom studies.

| | | Five DTPA patients | | Five MAG3 patients | | Three phantom simulations | |
|---|---|---|---|---|---|---|---|
| | | Average (cps) | SD | Average (cps) | SD | Average (cps) | SD |
| Heart | max | 181.8 | 71.9 | 118.6 | 29.6 | 155.0 | 15.5 |
| | min | 23.8 | 7.7 | 8.8 | 4.9 | 11.7 | 6.4 |
| | integral | 58619 | 16884 | 32913 | 11021 | 30519 | 21254 |
| Left kidney | max | 87.6 | 29.7 | 138.2 | 48.4 | 162.3 | 4.0 |
| | min | 39.4 | 20.1 | 31.0 | 12.2 | 41.0 | 8.5 |
| | integral | 84696 | 33411 | 108594 | 31247 | 141764 | 64079 |
| Right kidney | max | 117.0 | 37.3 | 154.2 | 87.5 | 147.0 | 77.5 |
| | min | 61.0 | 41.8 | 21.4 | 17.5 | 50.3 | 22.3 |
| | integral | 118386 | 56804 | 128038 | 96755 | 134377 | 71217 |
| Liver | max | 59.8 | 27.2 | 64.6 | 17.2 | 28.0 | 2.6 |
| | min | 15.6 | 5.5 | 14.6 | 4.5 | 21.7 | 7.4 |
| | integral | 37087 | 12326 | 42012 | 7224 | 37253 | 4523 |
| Spleen | max | 62.8 | 22.0 | 41.4 | 5.5 | 20.7 | 8.1 |
| | min | 16.2 | 4.5 | 7.8 | 2.6 | 17.0 | 11.3 |
| | integral | 38663 | 9307 | 24606 | 3595 | 26418 | 10704 |
| Background | max | 19.4 | 5.6 | 14.6 | 2.1 | 12.3 | 5.8 |
| | min | 10.2 | 3.6 | 4.8 | 2.4 | 9.3 | 8.4 |
| | integral | 22046 | 6503 | 13908 | 3130 | 16000 | 8310 |
| Bladder | max | 139.2 | 52.9 | 252.8 | 75.4 | 271.5 | 17.7 |
| | min | 10.6 | 23.7 | 0.0 | 0.0 | 4.0 | 5.7 |
| | integral | 132843 | 41836 | 269456 | 94789 | 194357 | 9786 | cps = counts per second

TABLE 4

The results of the three repeated phantom simulations I and III.

| | | Average | | | | SD | | | |
|---|---|---|---|---|---|---|---|---|---|
| | CV (%) | PI, left | PI, right | PIII, left | PIII, right | PI, left | PI, right | PIII, left | PIII, right |
| Area (cm$^2$) | 1.9 | 41.8 | 39.8 | 52.7 | 36.3 | 1.3 | 0.4 | 0.7 | 0.8 |
| Max count rate (cps) | 16.5 | 1139.0 | 968.0 | 1443.7 | 842.0 | 202.4 | 138.1 | 226.6 | 140.1 |
| Perfusion integral (%) | 5.5 | 47.7 | 52.3 | 84.0 | 16.0 | 3.8 | 3.8 | 1.0 | 1.0 |
| T$_{max}$ (min) | 2.1 | 4.3 | 2.7 | 3.0 | 6.8 | 0.0 | 0.0 | 0.0 | 0.2 |
| MTT (min) | 10.8 | 6.3 | 5.8 | 5.0 | 7.9 | 0.7 | 0.5 | 1.0 | 0.3 |
| Function Patlak (%) | 2.3 | 51.7 | 48.3 | 76.3 | 23.7 | 1.5 | 1.5 | 0.6 | 0.6 |
| Outflow index (%) | 1.2 | 86.0 | 80.3 | 91.0 | 69.7 | 1.0 | 1.2 | 1.0 | 0.6 |

TABLE 4-continued

The results of the three repeated phantom simulations I and III.

|  | | Average | | | | SD | | | |
| --- | --- | --- | --- | --- | --- | --- | --- | --- | --- |
|  | CV (%) | PI, left | PI, right | PIII, left | PIII, right | PI, left | PI, right | PIII, left | PIII, right |
| $T_{1/2}$ (min) | 5.0 | 9.1 | 17.7 | 3.8 | 9.0 | 0.3 | 0.9 | 0.2 | 0.3 |
| 20 min/max | 4.3 | 0.35 | 0.51 | 0.22 | 0.43 | 0.01 | 0.01 | 0.01 | 0.03 |

CV = coefficient variation, SD = standard deviation.
PI and PIII are phantom simulations I and III.
Area = region of interest of the kidney, Outflow index = percentage of injected tracer which has been excreted at 20 min.
$T_{max}$ = time to reach maximum activity, cps = counts per second, MTT = mean transit time, $T_{1/2}$ = time from maximal to half activity.
Perfusion integral and Function Patlak are parameters defined by Hermes (Nuclear Diagnostics AB. Hägersten, Sweden).
20 min/max = activity at 20 min divided by the maximum activity.

TABLE 5

The comparison of the measured parameters and the values estimated from the time schedules.

|  | PI, left | Ref. | Difference (%) | PI, right | Ref. | Difference (%) | PIII, left | Ref. | Difference (%) | PIII, right | Ref. | Difference (%) |
| --- | --- | --- | --- | --- | --- | --- | --- | --- | --- | --- | --- | --- |
| $T_{max}$ (min) | 4.3 (4.4 ± 0.4) | 4.5 | 4.7 | 2.7 (2.8 ± 0.3) | 2.8 | 3.7 | 3.0 (3.0 ± 0.3) | 3.2 | 6.7 | 6.8 (7.0 ± 0.4) | 6.6 | −2.9 |
| $T_{1/2}$ (min) | 9.1 | 9.9 | 8.8 | 17.7 | 25.2 | 42.6 | 3.8 | 4.1 | 7.9 | 9.0 | 12.0 | 3.33 |
| 20 min/max | 0.35 | 0.36 | 2.9 | 0.51 | 0.55 | 7.8 | 0.22 | 0.24 | 9.1 | 0.43 | 0.47 | 9.3 |

PI and PIII are phantom simulations I and III.
Figures in parentheses are the $T_{max}$ results of the multicentre comparison between 19 laboratories (average ± SD).
$T_{max}$ = time to reach maximum activity, $T_{1/2}$ = time from maximal to half activity.
20 min/max = activity at time 20 min divide by the maximum activity.
Ref. = value defined from the time schedule.

I claim:

1. An apparatus for calibration and/or quality assurance of nuclear medicine imaging, in which functional information of the organs to be studied is achieved by inserting radioactive solution emitting detectable radiation and by detecting the radiation by a gamma camera, comprising a phantom functionally simulating the organs to be studied, characterized in that the that the organs to be simulated by the phantom are in form of containers filled with radioactive solution, the apparatus further comprising movable isolating parts between the containers and the gamma camera to isolate radiation from the containers to the camera.

2. The apparatus according to claim 1 wherein the organs to be simulated by the phantom is the heart, the kidneys and/or the bladder.

3. The apparatus according to claim 1 wherein the containers simulating the organs to be studied are covered by lead and having organ-shaped holes for the radiation to be emitted.

4. The apparatus according to claim 1 wherein the movable parts for isolating the radiation are steel plates.

5. The apparatus according to claim 1 wherein it comprises a background container simulating the shapes of the spleen, the liver and the outlines of the soft tissues for visual purposes.

6. The apparatus according to claim 5 wherein there is a movable lead plate between the background container and the gamma camera for regulation and isolation of the radiation from the phantom.

7. The apparatus according to claim 1 wherein there is a cartridge comprising a plastic tube filled with radioactive liquid simulating the ureters.

8. The apparatus according to claim 4 wherein the steel plates are moving in accordance with a preset time schedule forth and back to the space between the kidneys and the background for sumulating the filling and washout of the kidneys.

9. The apparatus according to claim 2 wherein the phantom comprises an attenuator circulating at a preset rate to simulate the central circulation of the radioactive solution through the heart.

10. The apparatus according to claim 2 wherein the phantom comprises an attenuator circulating at a preset rate to mimic filling of the bladder.

11. The apparatus according to claim 2 wherein simulate the central circulation of the radioactive solution through the heart by means of steel plates moving in accordance with a preset time schedule.

12. The apparatus according to claim 2 wherein filling of the bladder is simulated by means of steel plates moving in accordance with a preset time schedule.

13. The apparatus according to claim 2 wherein the moving parts are controlled by using computerized step motors.

14. The apparatus according to claim 2 wherein the functions and the shape of the kidneys is automated.

* * * * *